(12) United States Patent
Dent et al.

(10) Patent No.: US 10,621,306 B2
(45) Date of Patent: Apr. 14, 2020

(54) PHARMACEUTICAL TRAY FILING SYSTEM AND METHOD

(71) Applicant: ARxIUM, Inc., Buffalo Grove, IL (US)

(72) Inventors: Jacob A. Dent, Wildwood, IL (US); Syed Sabih Jafri, Morton Grove, IL (US); Michaela McGill, Gurnee, IL (US)

(73) Assignee: ARxIUM, Inc., Buffalo Grove, IL (US)

( * ) Notice: Subject to any disclaimer, the term of this patent is extended or adjusted under 35 U.S.C. 154(b) by 679 days.

(21) Appl. No.: 15/277,476

(22) Filed: Sep. 27, 2016

(65) Prior Publication Data

US 2017/0017775 A1 Jan. 19, 2017

Related U.S. Application Data

(62) Division of application No. 13/828,791, filed on Mar. 14, 2013, now Pat. No. 9,477,816.

(51) Int. Cl.
*G16H 20/10* (2018.01)
*G16H 20/13* (2018.01)
*G06F 19/00* (2018.01)

(52) U.S. Cl.
CPC ................ *G06F 19/3462* (2013.01)

(58) Field of Classification Search
CPC .................... B65B 5/103; G06F 19/3462
See application file for complete search history.

(56) References Cited

U.S. PATENT DOCUMENTS

| 7,293,672 | B2 * | 11/2007 | Mori | B65B 5/103 |
| | | | | 221/122 |
| 7,878,369 | B2 * | 2/2011 | Kobayashi | A47B 88/956 |
| | | | | 221/197 |
| 8,380,346 | B2 * | 2/2013 | Chudy | G06F 19/3462 |
| | | | | 700/242 |
| 2001/0002448 | A1 | 5/2001 | Wilson et al. | |
| 2002/0153056 | A1 | 10/2002 | Siegel et al. | |
| 2003/0057231 | A1 * | 3/2003 | Kim | B65B 5/103 |
| | | | | 221/263 |

(Continued)

OTHER PUBLICATIONS

International Preliminary Report on Patentability for International Application No. PCT/US2014/024807 dated Sep. 24, 2015, 11 pages.

(Continued)

*Primary Examiner* — Andrew M Tecco
*Assistant Examiner* — Eyamindae C Jallow
(74) *Attorney, Agent, or Firm* — Reinhart Boerner Van Deuren s.c.

(57) ABSTRACT

A system for facilitating the manual filling of a pharmaceutical tray is provided. The system includes an electronic display device configured to display information adjacent the wells of the pharmaceutical tray. The system includes a controller configured to control the electronic display device to display information representative of a first type of pharmaceutical adjacent to a first well to direct manual placement of the first type of pharmaceutical into the first well and to control the electronic display device to selectively display information representative of a second type of pharmaceutical adjacent to a second well to direct manual placement of the second type of pharmaceutical into the second well.

10 Claims, 9 Drawing Sheets

(56) References Cited

U.S. PATENT DOCUMENTS

| | | | | |
|---|---|---|---|---|
| 2004/0084512 A1* | 5/2004 | Inamura | B65B 5/103 | 229/87.01 |
| 2004/0134043 A1* | 7/2004 | Uema | G07F 11/62 | 24/297 |
| 2004/0176873 A1* | 9/2004 | Kim | G07F 11/44 | 700/231 |
| 2005/0145644 A1* | 7/2005 | Mori | B65B 5/103 | 221/242 |
| 2006/0230710 A1* | 10/2006 | Ishiwatari | B65B 5/103 | 53/493 |
| 2009/0044489 A1* | 2/2009 | Siegel | B65B 5/103 | 53/247 |
| 2009/0152291 A1* | 6/2009 | Ohmura | A61J 7/0084 | 221/197 |
| 2009/0223592 A1 | 9/2009 | Procyshyn et al. | | |
| 2009/0321469 A1* | 12/2009 | Knoth | B65B 5/103 | 221/7 |
| 2009/0321470 A1* | 12/2009 | Knoth | B65B 5/103 | 221/7 |
| 2010/0077707 A1* | 4/2010 | Kondo | B65B 5/103 | 53/493 |
| 2010/0121486 A1* | 5/2010 | Yuyama | G07F 11/44 | 700/227 |
| 2011/0015782 A1 | 1/2011 | Chudy et al. | | |
| 2011/0094327 A1* | 4/2011 | Knoth | B65B 5/103 | 74/490.09 |
| 2011/0131056 A1 | 6/2011 | Chudy et al. | | |
| 2011/0160901 A1* | 6/2011 | Abrams, Jr. | G07F 11/44 | 700/232 |
| 2011/0303692 A1* | 12/2011 | Kim | B65B 5/103 | 221/1 |
| 2012/0253839 A1* | 10/2012 | Berzansky | G06Q 10/06 | 705/2 |
| 2012/0259457 A1 | 10/2012 | Hanfield et al. | | |
| 2012/0324829 A1* | 12/2012 | Omura | B65B 1/28 | 53/147 |
| 2013/0018503 A1 | 1/2013 | Carson et al. | | |
| 2013/0126545 A1 | 5/2013 | Chudy et al. | | |
| 2013/0158706 A1 | 6/2013 | Chudy et al. | | |
| 2013/0218330 A1 | 8/2013 | Chudy et al. | | |

OTHER PUBLICATIONS

FastPak® EXP Operating Manual, Chapter 4, AmerisourceBergen Technology Group, copyrighted 2012, 10 pages.

AmerisourceBergen the Best Medicine for Healthcare, FastPak EXP, http://www.amerisourcebergendrug.com/abcdrug/Videos/FastpakEXP_Web/FastpakEXP.html, website with an interactive video showing the FastPak EXP, showing FastPak EXP system which was commercially available before Mar. 14, 2012.

Willach Pharmacy Solutions, "CONSIS.B Fast, compact, efficient. CONSIS robotic dispensers", publically available at http://www.willach-pharmacy-solutions.com/en/products/ before Apr. 23, 2013, Consis device on p. 5 was commercially available before Mar. 14, 2012.

AmerisourceBergen Technology Group, "FastPak EXP High-Volume Oral Solid Packaging", brochure available at http://www.amerisourcebergendrug.com/abcdrug/our_solutions/technology_solutions/Packaging/index.jsp, showing FastPak EXP system which was commercially available before Mar. 14, 2012.

* cited by examiner

PHARMACEUTICAL TRAY FILING SYSTEM AND METHOD

CROSS-REFERENCE TO RELATED PATENT APPLICATION

This application is a divisional of Ser. No. 13/828,791, filed Mar. 14, 2013, which is incorporated herein by reference in its entirety.

BACKGROUND OF THE INVENTION

The present invention relates generally to the field of pharmaceutical packaging and distribution. The present invention relates specifically to a filing of a pharmaceutical tray. Automated packaging devices are used by various health care and pharmacy operations to accurately package pharmaceuticals for use within the facility. For example, multiple pharmaceuticals for a patient may be packaged together. The packaged pharmaceuticals are then provided to the patient

SUMMARY OF THE INVENTION

One embodiment of the invention relates to pharmaceutical filling system including a display screen configured to display instructions to a user of the workstation, a flat panel display screen and a tray support structure located at a peripheral edge of the flat panel display screen. The system includes a tray including a plurality of wells, and each well is configured to hold a pharmaceutical. Each well including a bottom wall formed from a light transmitting material. The tray is positioned on and supported by the tray support structure above the flat panel display screen. The system includes a controller configured to control the flat panel display screen to display information related to a first pharmaceutical at a first region of the flat panel display screen such that the displayed information is viewable from above the tray through the bottom wall of a first well of the tray to direct the user of the workstation to fill the first well with the first pharmaceutical.

Another embodiment of the invention relates to a system for facilitating the manual filling of a pharmaceutical tray including at least two wells each configured to hold a pharmaceutical. The system includes an electronic display device configured to display information adjacent to the at least two wells of the pharmaceutical tray. The system includes a controller configured to control the electronic display device to display information representative of a first type of pharmaceutical adjacent to a first well to direct manual placement of the first type of pharmaceutical into the first well and to control the electronic display device to selectively display information representative of a second type of pharmaceutical adjacent to a second well to direct manual placement of the second type of pharmaceutical into the second well.

Another embodiment of the invention relates to a method of controlling a pharmaceutical filling workstation to facilitate the manual filling of a pharmaceutical tray including a plurality of wells each configured to hold a pharmaceutical. The method includes the step of controlling a display device to display information indicative of a first pharmaceutical below a first well of the plurality of wells. The method includes the step of receiving a first input indicative of the first pharmaceutical being placed in the first well. The method includes the step of controlling the display device to display information indicative of a second pharmaceutical below a second well of the plurality of wells. The method includes the step of receiving a second input indicative of the second pharmaceutical being placed in the second well.

Another embodiment of the invention relates to a system for filling a prescription medication orders. The system includes a medication tray including at least one row of medication channels passing through the tray and a unique machine-readable tray identifier. The system includes a workstation including a first display device configured to display medication information and to display information input at the workstation. The workstation also includes a second display configured to display images at the bottom of a plurality of channels and a reader assembly configured to read the tray identifier and to read a machine-readable medication identifier from a medication container. The system includes a database including tray data representative of the tray identifier, data representative of medication items to be manually placed in the medication tray, and data representative of the respective channels within which the respective medication items are to be placed. The database includes prescription data representative of information for a plurality of medication items where such information includes data useable by the workstation to generate of images of a plurality of medication items on the first and second displays. The database includes association data which associates the medication identifier with the medication items. The workstation is configured to communicate with the database and the reader assembly, to display information on the first display representative of at least one medication item associated with a tray identifier, to display information on the first display representative of medication from a medication container and to generate an image representative of the medication item at the bottom of the channel in the tray at which the medication item is to be placed.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION

Referring generally to the figures, various embodiments of a pharmaceutical filling system configured to facilitate filing (e.g., manual filing) of a multi-compartment pharmaceutical tray and related method are shown. Generally, the tray includes multiple compartments or wells each configured to hold one or more medication/pharmaceutical items and/or one or more medical items, and the tray typically is filled with more than one different type of pharmaceutical item at a time. The system includes a display device configured to display information representative of each type of pharmaceutical adjacent to the wells/channels of the tray in a manner that directs the filling of the well with the appropriate pharmaceutical.

In some embodiments, the system includes a filling workstation having a tray support device. The tray support device includes a display device surrounded by a support housing such that the display screen is positioned below the tray during filling. During the tray filling processing, the display device displays information (e.g., images, alphanumeric information, etc.) in various positions on the display device such that the information displayed is viewable through the bottom wall of the wells of the tray. The information displayed provides an indication of the type of pharmaceutical that is to be placed within the well through which the information is viewable. During filling of the tray, the user (e.g., health care personnel, pharmacist, pharmacy technician, etc.) is able to see the displayed information displayed below each well and places the pharmaceutical that corresponds with the displayed information into the well. Following filling of the tray with the appropriate pharmaceutical in each well, the filled tray may be used to load the pharmaceuticals into an automated packaging system which then packages each of the loaded pharmaceuticals into the desired packaging (e.g., unit dose packaging, packaging along with other pharmaceuticals for a particular patient, belt packages, etc.).

Figure 1:
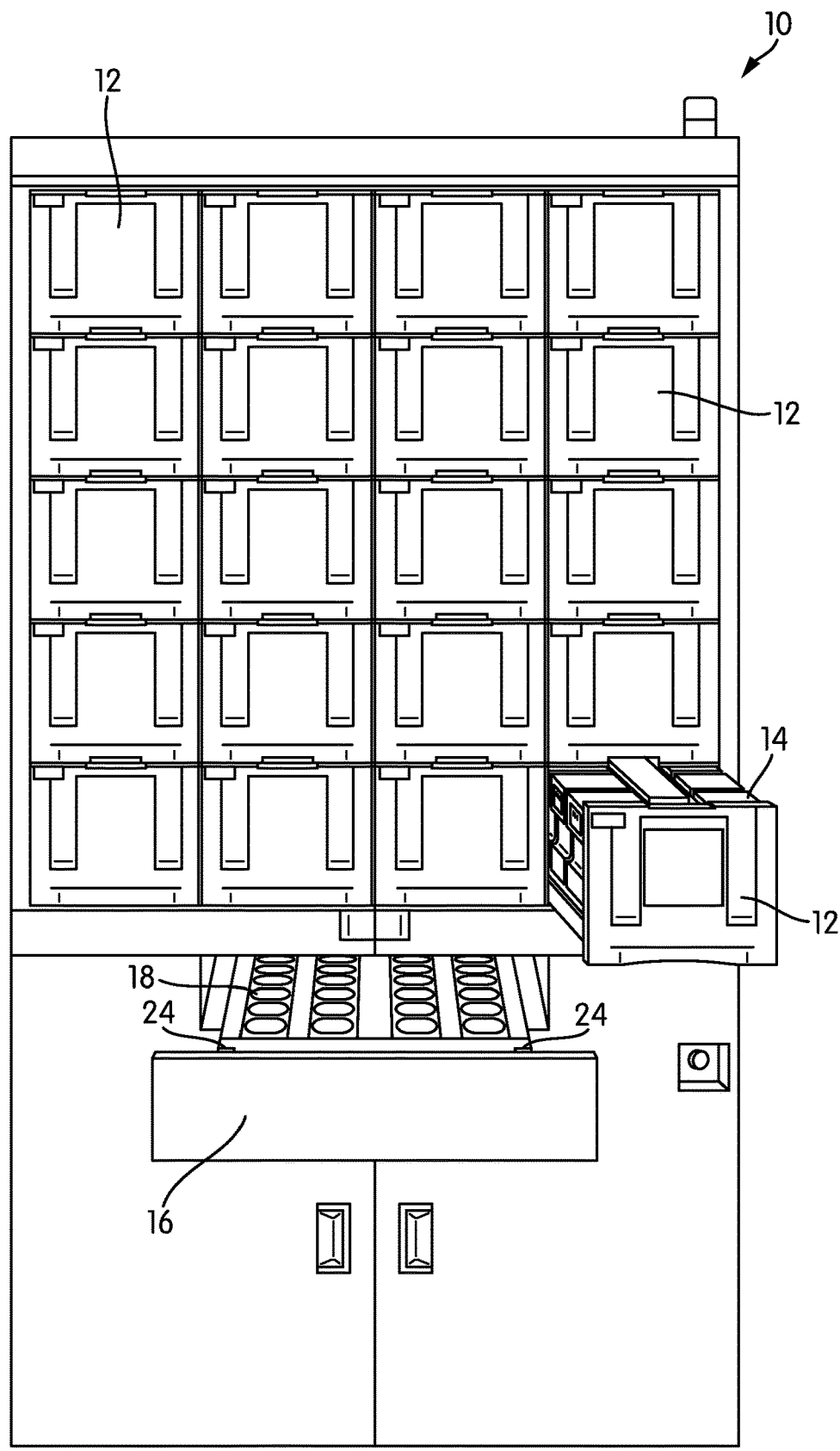
FIG. 1 is a packaging cabinet and pharmaceutical tray according to an exemplary embodiment.

Referring to FIG. 1, an automated packaging system, shown as packaging cabinet 10, is shown according to an exemplary embodiment. Cabinet 10 includes a plurality of pharmaceutical canister dispensing compartments 12. Each compartment 12 holds a plurality of pharmaceutical canisters 14 that each hold a single type of pharmaceutical. Compartments 12 typically are loaded with canisters 14 containing the pharmaceuticals that are most commonly used by the facility (e.g., hospital, pharmacy, long-term care facility, nursing home, etc.). Cabinet 10 also includes a dispensing drawer 16 that includes a plurality of cells or wells 18. Wells 18 of dispensing drawer 16 are typically filled with pharmaceuticals that are used less frequently by the facility than the pharmaceuticals stored in compartment 12. The positioning of each pharmaceutical within cabinet 10 (e.g., the positioning of each canister 14 and the identity of each pharmaceutical located with wells 18 of drawer 16) is tracked and stored by the electronic control system controlling cabinet 10 such that the desired pharmaceutical can be dispensed and packaged as needed.

With compartments 12 and drawer 16 filled, cabinet 10 is used to individually package pharmaceuticals based on prescription information received by the cabinet. In one particular embodiment, cabinet 10 is configured to dispense the appropriate type and quantity of the different pharmaceuticals that make up a prescription for a patient and to package the pharmaceuticals in a strip-type package. In one particular embodiment, cabinet 10 is a FastPak EXP available from AmerisourceBergen Technology Group.

Figure 2:
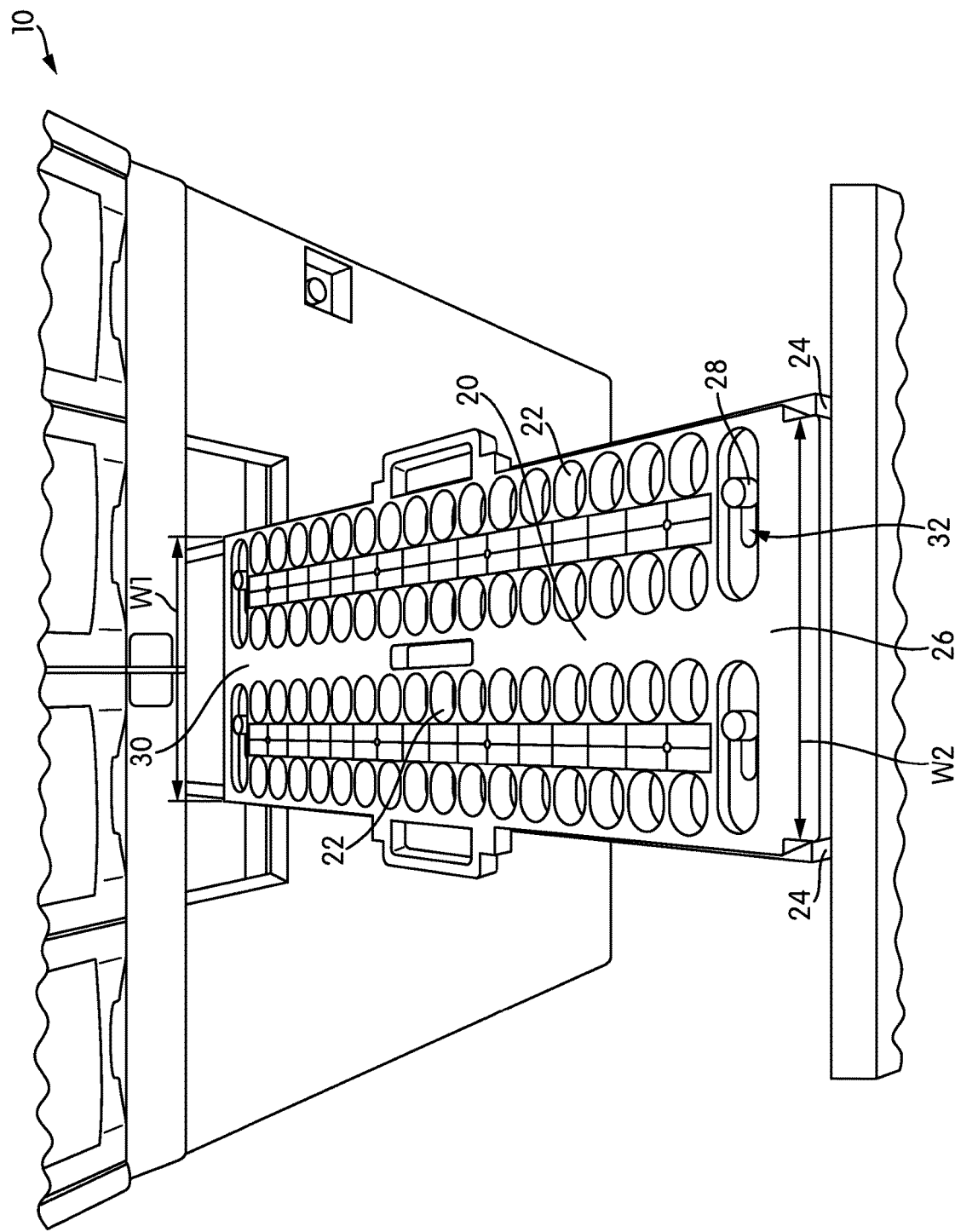
FIG. 2 is the packaging cabinet of FIG. 1 with the tray supported on a drawer of the cabinet according to an exemplary embodiment.

Referring to FIG. 1, a multi-chamber tray, shown as tray 20, may be used to facilitate the filling of each of the wells 18 of dispensing drawer 16. In the embodiment shown, tray 20 includes a plurality of numbered wells/channels 22 that corresponded to wells 18 of dispensing drawer 16. As explained in more detail below, wells 22 of tray 20 are filled with the proper pharmaceutical to be placed into the corresponding wells 18 of drawer 16. As shown in FIG. 2, with tray 20 filled, tray 20 is placed onto drawer 16 such that each well 22 of tray 20 is located above the corresponding well 18 of drawer 16. In one embodiment, drawer 16 includes an alignment feature that aligns tray 20 relative to drawer 16 in the proper orientation to ensure that the each well 22 of tray 20 is positioned above the proper well 18 of drawer 16. In the embodiment shown, drawer 16 includes a rim 24 that extends inward from the lateral edges of drawer 16, and tray 20 includes a first lateral edge, shown as narrow end 26, and a second lateral edge, shown as wide end 30. As shown in FIG. 2, the width, W2, of narrow end 26 is less than the width, W1, of wide end 30. Narrow end 26 is sized to fit between rim 24 of drawer 16 such that tray 20 is permitted to properly seat on drawer 16 only when narrow end 26 is located between rim 24. This arrangement helps to ensure that tray 20 is properly oriented relative to drawer 16 such that each well 22 of tray 20 is positioned above the proper, corresponding well 18 of drawer 16.

With tray 20 properly positioned on drawer 16, levers 28 are actuated causing the bottom walls/panels which close wells 22 to slide open allowing the pharmaceutical within each well 22 to fall into the corresponding well 18 of drawer 16. In one embodiment, tray 20 includes a single planar wall on each half of tray 20 that extends along the lower surface of tray 20, and the wall forms the bottom wall of all of the wells 22 on each half of tray 20. Levers 28 on each half of tray 20 are coupled to the walls such that as levers 28 are moved laterally within slot 32, the bottom walls are moved out from under wells 22 allowing the pharmaceutical within each well 22 to fall into the corresponding well 18 of drawer 16. Once drawer 16 is filled, tray 20 is removed from on top of drawer 16, and drawer 16 is retracted into the body of cabinet 10. Cabinet 10 is then ready to dispense the pharmaceuticals from drawer 16 as needed.

Figure 3:
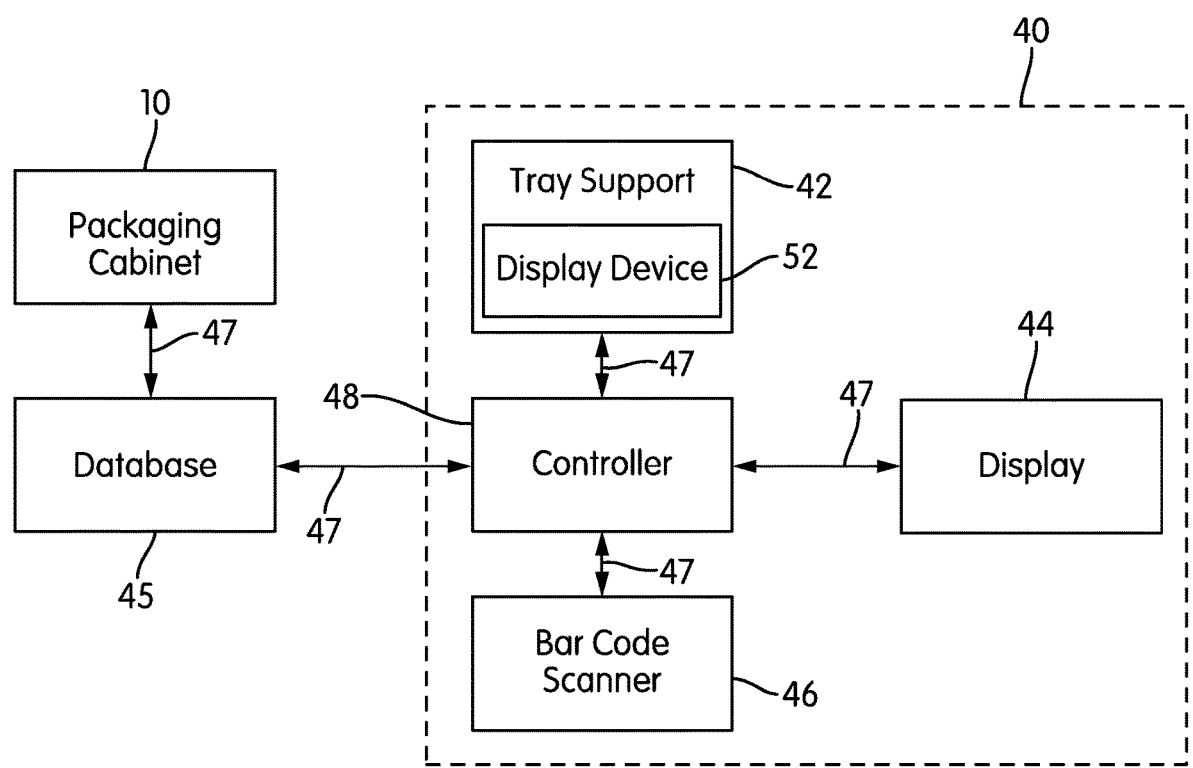
FIG. 3 is a block diagram of a filling workstation according to an exemplary embodiment.

In one embodiment, as shown in FIGS. 3-6, tray 20 may be filled at a workstation, shown as tray filling workstation 40. Filling workstation 40 includes a tray support structure, shown as tray support 42, a first display 44 and a reader, shown as bar code scanner 46. As shown in the diagram of FIG. 3, filling workstation 40 also includes a control system, shown as controller 48, configured to control the various components of filling workstation 40 to provide the functionality discussed herein. As shown, controller 48 is communicably coupled to packaging cabinet 10 and database 45. Communication links 47 provide communication between the different devices shown in FIG. 3. Communication between packaging cabinet 10, database 45 and controller 48 allows information regarding which pharmaceuticals are to be filled into a tray to be communicated between cabinet 10, database 45 and controller 48 at filling workstation 40. In addition, various information from workstation 40 (e.g., identification information for each filled tray 20, error code information, etc.) may be communicated between cabinet 10, database 45 and controller 48. In various embodiments, database 45 may use the information communicated from workstation 40 to identify a particular tray 20, to identify the particular pharmaceuticals loaded into tray 20, and to identify the particular well 22 of the tray that includes the particular pharmaceutical. This information may be used by database 45 and the related control software to control cabinet 10 to properly package the pharmaceuticals as needed. In one embodiment, database 45 acts as a server and packaging cabinet 10 and workstation 40 are clients of database 45. It should be understood that while FIG. 3 shows a single packaging cabinet 10 and a single workstation served by database 45, multiple packaging cabinets 10 and/or multiple workstations 40 may be used in conjunction with database 45.

Controller 48 may be a general purpose computer, a general purpose processor, an application specific processor (ASIC), a circuit containing one or more processing components, a group of distributed processing components, a group of distributed computers configured for processing, etc., configured to provide the functionality of workstation 40 discussed herein. Controller 48 may include or have access to one or more devices for storing data and/or computer code for completing and/or facilitating the various processes described in the present application. Such storage devices may include volatile memory, non-volatile memory, database components, object code components, script components, and/or any other type of information structure for supporting the various functions of workstation 40 described herein. In various embodiments, controller 48 is a desktop or laptop computer including software configured to provide the functionalities of workstation 40 discussed herein. Communication links 47 may be wired or wireless communication links and may use either standard or proprietary communications protocols, and controller 48 is configured with appropriate hardware and/or software for communicating with the devices shown in FIG. 3.

Figure 4:
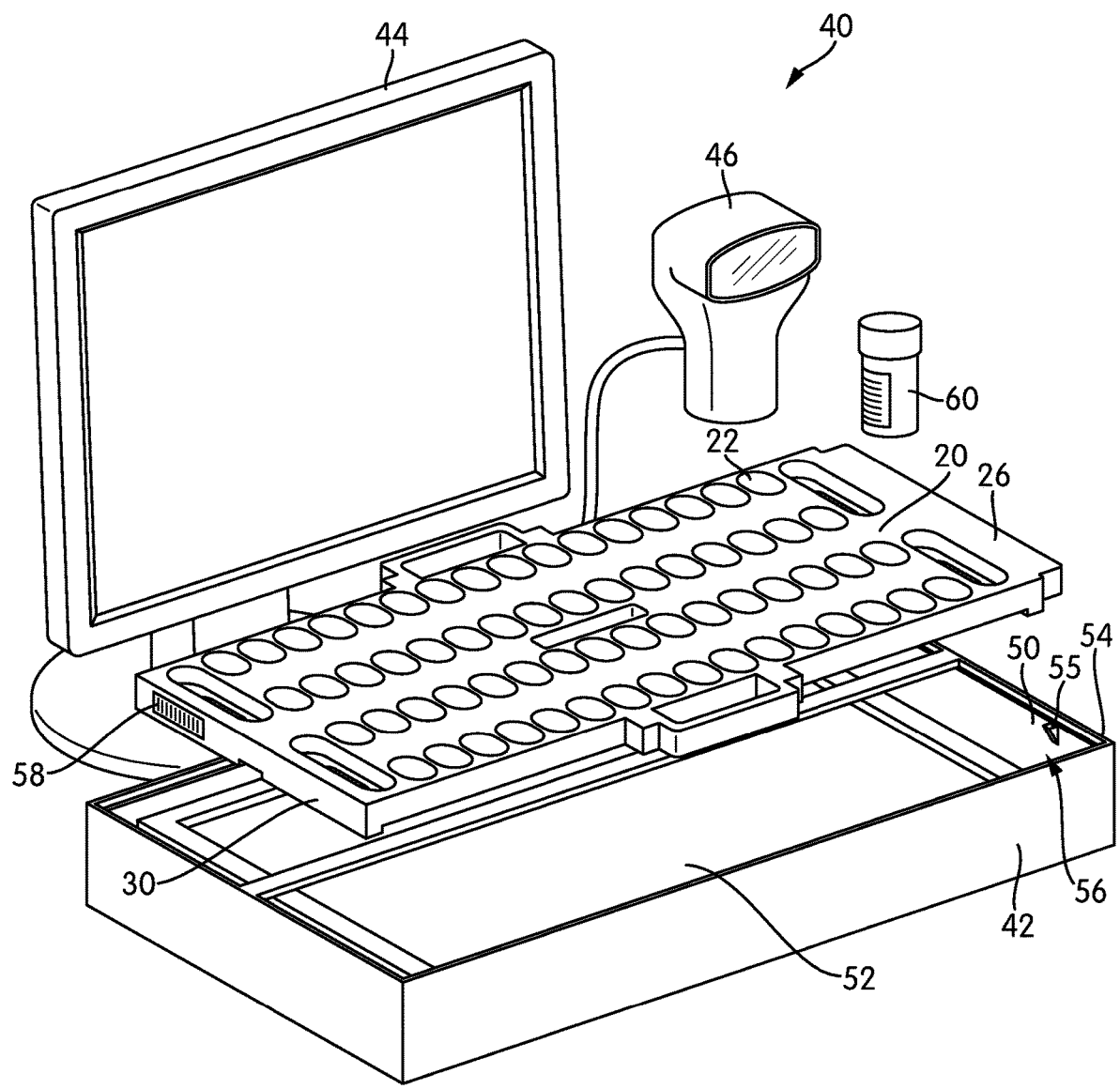
FIG. 4 is a filling workstation according to an exemplary embodiment.
Figure 5:
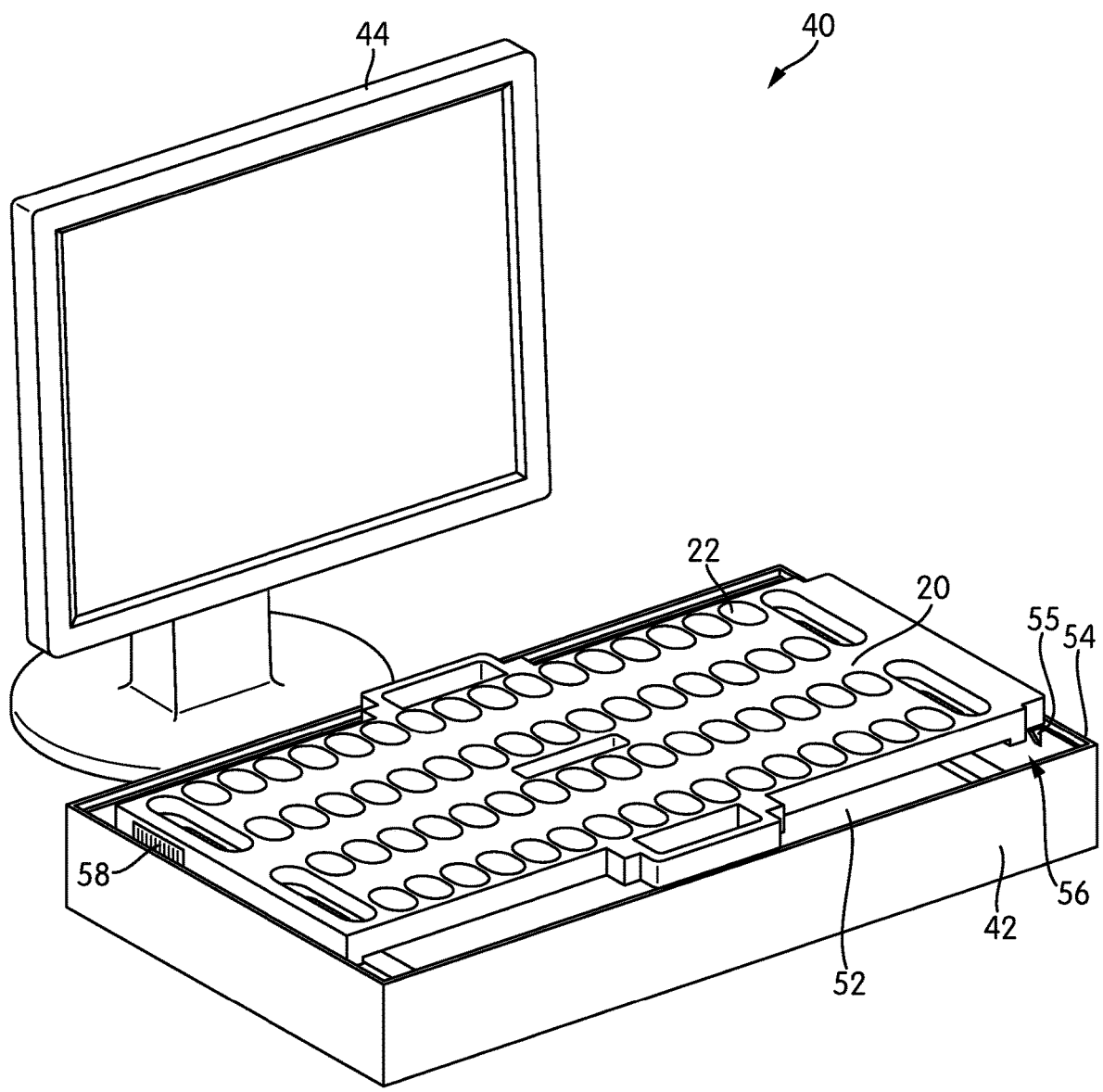
FIG. 5 is the filling workstation of FIG. 4 with a pharmaceutical tray supported above a display device according to an exemplary embodiment.

Referring to FIG. 4, tray support 42 includes a support housing 50 and a second display 52. In various embodiments, second display 52 is a display device including a flat panel display screen, and for example, is an LCD display device or LED screen display device. As shown in FIG. 4, the flat panel of the display 52 lies in a substantially horizontal plane (e.g., a plane less than plus or minus 45 degrees from horizontal, less than plus or minus 45 degrees from horizontal, plus or minus 10 degrees from horizontal, etc.). As shown in FIG. 5, prior to filling, tray 20 is placed on to tray support 42. Tray support 42 includes a physical structure that orients tray 20 over display 52 in a way that display 52 is viewable from above tray 20. In the specific embodiment shown, support housing 50 includes an upstanding peripheral rim 54 that extends upward and away from a support surface 56. In this embodiment, support surface 56 is a substantially horizontal support surface extending inwardly from an inner surface of peripheral rim 54. In the tray fill position shown in FIG. 5, a lower surface of tray 20 seats on support surface 56, and the inner surface of peripheral rim 54 engages the outer, lateral surface of tray 20 to securely seat tray 20 on tray support 42. In this arrangement, peripheral rim 54 surrounds the peripheral edge of display 52.

In various embodiments, tray support 42 includes an alignment structure configured to engage tray 20 such that tray 20 is only permitted to seat tray support 42 in the proper positioning. In the embodiment shown in FIG. 5, peripheral rim 54 of tray support 42 includes an inset region 55 sized to engage narrow end 26 of tray 20. To properly mount tray 20 to tray support 42, narrow end 26 of tray 20 is placed within inset region 55 of peripheral rim 54, and if the user attempts to mount tray support 42 in an incorrect orientation, inset region 55 interferes with wide end 30 of tray 20 providing a visual indication that tray 20 is not mounted in the correct orientation. In another embodiment, the alignment feature is a dowel pin that engages a bushing only when tray 20 is loaded onto tray support 42 in the proper position. In another embodiment, the alignment feature is an electronic tag reader that reads a tag on tray 20 only when tray 20 is loaded onto tray support 42 in the proper position.

Tray 20 also includes a identification tag, shown as tray barcode 58, that uniquely identifies tray 20. Barcode 58 will be read prior to filling tray 20 with pharmaceuticals at workstation 40. The tray identification information read from barcode 58 is then associated with data indicating which pharmaceuticals are to be loaded into tray 20 (e.g., a tray fill order as discussed below), and thus, during loading of cabinet 10 the identity of tray 20 is read and information indicating which pharmaceuticals are loaded in each cell of tray 20 (and consequentially in each corresponding well of drawer 16) is stored within database 45 associated with cabinet 10 to track which pharmaceuticals have been loaded into cabinet 10. Database 45 and the related control software utilize the information indicating which pharmaceuticals are located in each cell of drawer 16 to control cabinet 10 to properly dispense the desired pharmaceutical from drawer 16 during packaging.

In one embodiment, barcode 58 may be read using an external barcode reader 46. In another embodiment, tray support 42 may include a barcode reader directly coupled to support housing 50. In this embodiment, workstation 40 is configured to automatically read the barcode upon mounting of tray 20 onto tray support 42. In another embodiment, the identification tag is an RFID tag, and tray support 42 includes an RFID reader. In another embodiment, the identification tag is a label including a unique alphanumeric code that the user of workstation 40 enters (e.g., via keyboard) prior to filling tray 20.

After tray 20 is seated onto tray support 42 and the ID tag of tray 20 is read, workstation 40 (e.g., under the control of controller 48) is configured to assist the user of workstation 40 to properly place the correct pharmaceuticals into wells 22 of tray 20. As discussed in more detail below, various information and instructions are displayed to the user via display 44 to guide the user through the tray filling process. For example, instructions to fill certain wells 22 of tray 20 with a particular pharmaceutical may be displayed on display 44. In one embodiment, the user of workstation 40 retrieves a container 60 of the needed pharmaceutical and scans a barcode on container 60 with scanner 46. Controller 48 of workstation 40 confirms that the proper pharmaceutical container was retrieved, and the user is instructed to fill one or more wells 22 of tray 20 with the pharmaceutical from container 60. When all required wells 22 of tray 20 have been filled from container 60, the user returns container 60 to storage and continues filling the remaining wells of tray 20 with the proper pharmaceuticals.

Figure 6:
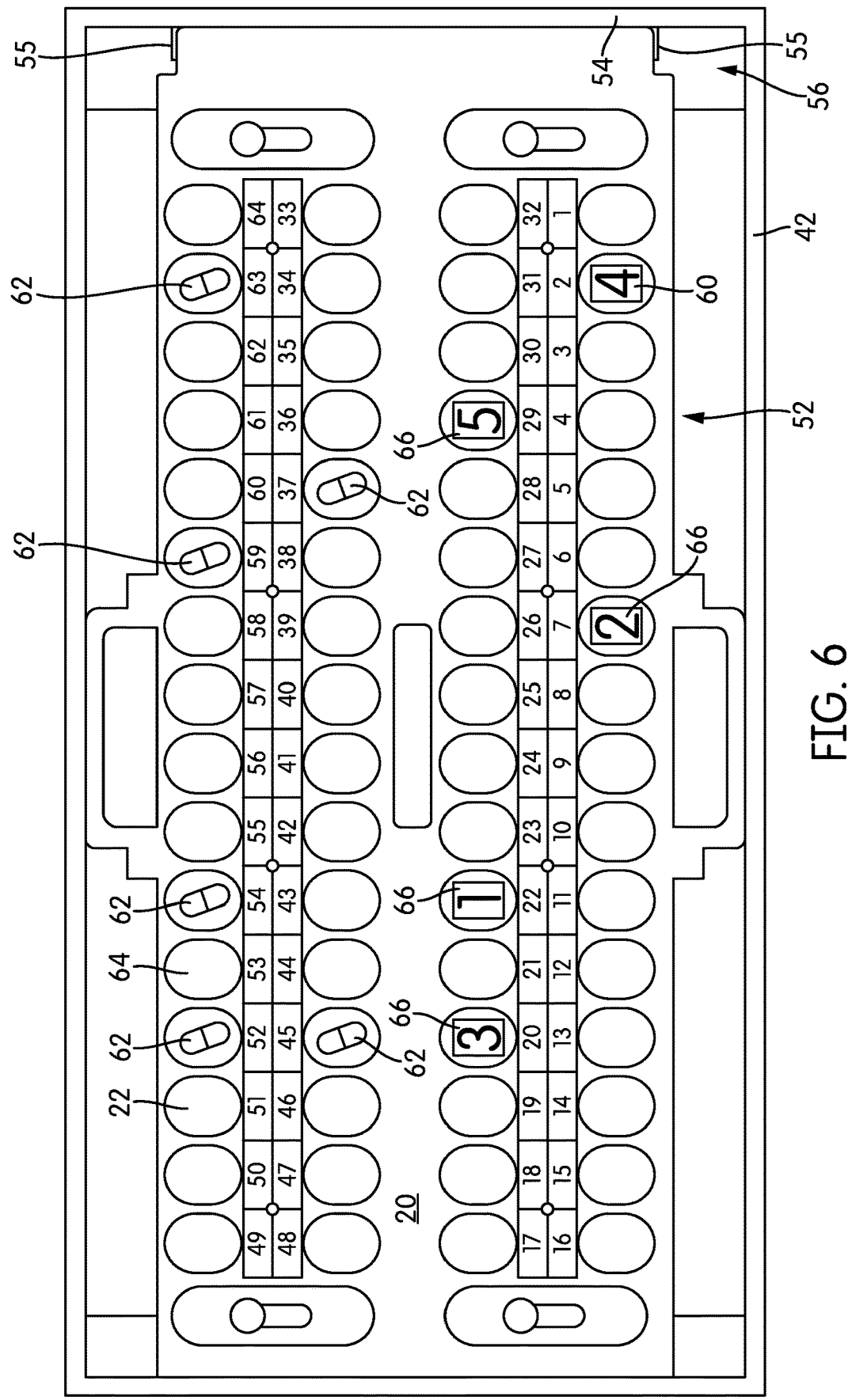
FIG. 6 is a top view of the pharmaceutical tray of FIG. 5 depicting display of information to facilitate filling of the pharmaceutical tray according to an exemplary embodiment.

Referring to FIG. 6, workstation 40 is configured to assist in filing tray 20 by causing the display of information representative of a particular pharmaceutical (e.g., display of an image and/or display of alphanumeric information) to direct the user of workstation 40 to fill particular wells 22 of tray 20 with a particular pharmaceutical. In various embodiments, workstation 40 includes one or more display devices, shown as display screen 52, configured to display the information adjacent to the particular wells 22 of tray 20 to be filled with a particular pharmaceutical. In one such embodiment, as shown in FIG. 6, display screen 52 is located below tray 20, and the controller of workstation 40 is configured to display one or more images 62 at distinct spatial positions on screen 52 such that the one or more images 62 are located below each well 22 of tray 20 that is to a particular pharmaceutical. In one embodiment, image 62 is an image of the particular pharmaceutical that is to be added to the well below which the image 62 is displayed. In the embodiment shown, each well 22 includes a lower wall 64 that transmits light (e.g., light transmitting. transparent or translucent) such that images 62 displayed on screen 52 are viewable from above tray 20. In another embodiment, a filling indication (e.g., a lighted or colored shaped, a white square, etc.) can be displayed on the flat panel display between each well 22 to direct the user to fill the appropriate well.

In addition to displaying pharmaceutical images, controller 48 of workstation 40 may be configured to cause the display of alphanumeric information 66 representative of a pharmaceutical (instead of or in addition to images 62) at distinct spatial positions on screen 52 such that the alphanumeric information 66 is located below each well 22 of tray 20 that is to receive the pharmaceutical currently being filled. As explained in more detail below, once a first set of wells 22 are filled, images 62 and/or alphanumeric information 66 may be displayed beneath another set of wells indicating that the user is to fill those cells with a second type of pharmaceutical. This process repeats until there are no other pharmaceuticals to be loaded into tray 20.

In one embodiment, image 62 displayed is an image of the particular pharmaceutical to be placed into the corresponding well 22 of tray 20. Thus, the user of workstation 40 is able to compare the appearance of the pharmaceutical actually being placed into tray 20 with the image 62 being displayed to confirm that the proper pharmaceutical is being loaded into tray 20. In another embodiment, image 62 may be a generic image or graphic displayed to highlight which well 22 of tray 20 is to be filled. In one embodiment, alphanumeric information 66 may be a drug code for the drug being filled or the name of the drug being filled. In another embodiment, alphanumeric information 66 may be show the number of individual pills or tablets that are to be placed in the associated well.

In various embodiments, controller 48 of workstation 40 is in communication with a database, shown as database 45, and database 45 includes various data that is used by controller 48 to provide the functionality discussed herein. Database 45 is also in communication with cabinet 10 and also may include control software for controlling cabinet 10. In various embodiments database 45 includes one or more of the following types of data: tray data representative of the tray identifier, data representative of pharmaceutical or medical items to be manually placed in the wells of the pharmaceutical tray, data representative of the respective wells within which the respective pharmaceutical or medical items are to be placed, data representative of the pharmaceutical or medical items, association data which associates the pharmaceutical or medical identifier with the pharmaceutical or medical items, alpha numeric data associated with the pharmaceutical or medical items, expiration dates associated with the pharmaceutical or medical items, manufacturer information associated with the pharmaceutical or medical items and any other information which may be required for a particular application. In various embodiments, the prescription data is representative of information for a plurality of pharmaceutical, medication or medical items where such information includes at least data useable by the workstation to generate images for the plurality of medication items on the first and second displays. In various specific embodiments, the data from database 45 may be used by workstation 40 to generate of images for a plurality of pharmaceutical items on displays 44 and/or 52.

In various embodiments, each well 22 of tray 20 may be equipped with a sensor configured to detect when the well has been filled. In one such embodiment, bottom wall 64 may be a touch sensitive sensor such that each pill impact within well 22 is detected and counted. In another embodiment, each well 22 may be equipped with an infrared reflectance sensor, a capacitance sensor or proximity sensor configured to detect entry of each pill into well 22.

In the embodiments discussed above, tray 20 and workstation 40 are described primarily relating to filling a tray with pharmaceuticals and/or medical items. However in other embodiments, a tray 20 and workstation 40 can generally be equipped and/or configured to facilitate placement of other items into a multi-welled tray. In such embodiments, the information (e.g., an image, alphanumeric-information, etc.) displayed adjacent or below each well of the tray is representative of the item to be placed in the well.

Figure 7A:
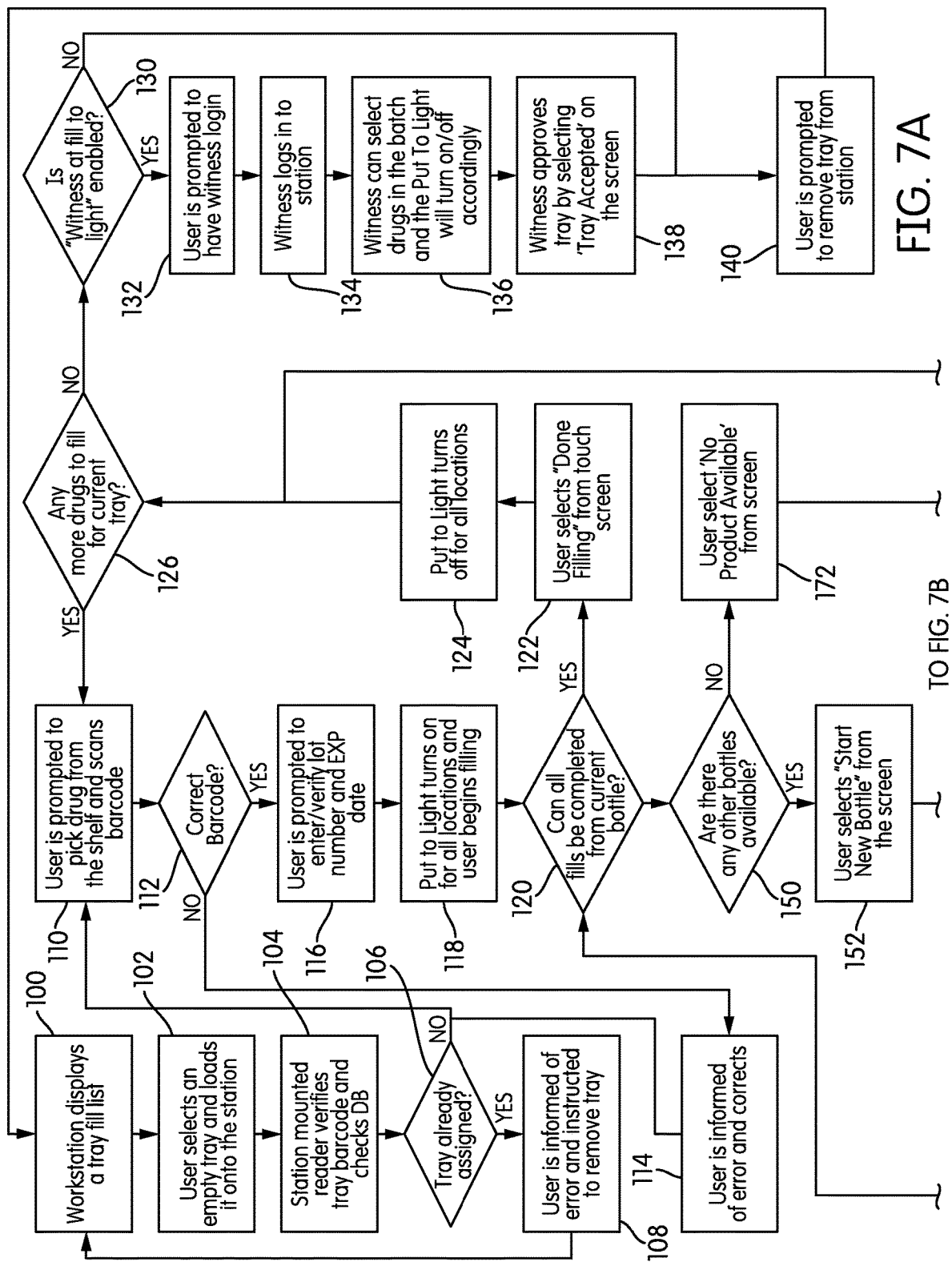
FIGS. 7A and 7B show a process of filling a pharmaceutical tray using a filling workstation according to an exemplary embodiment.
Figure 7B:
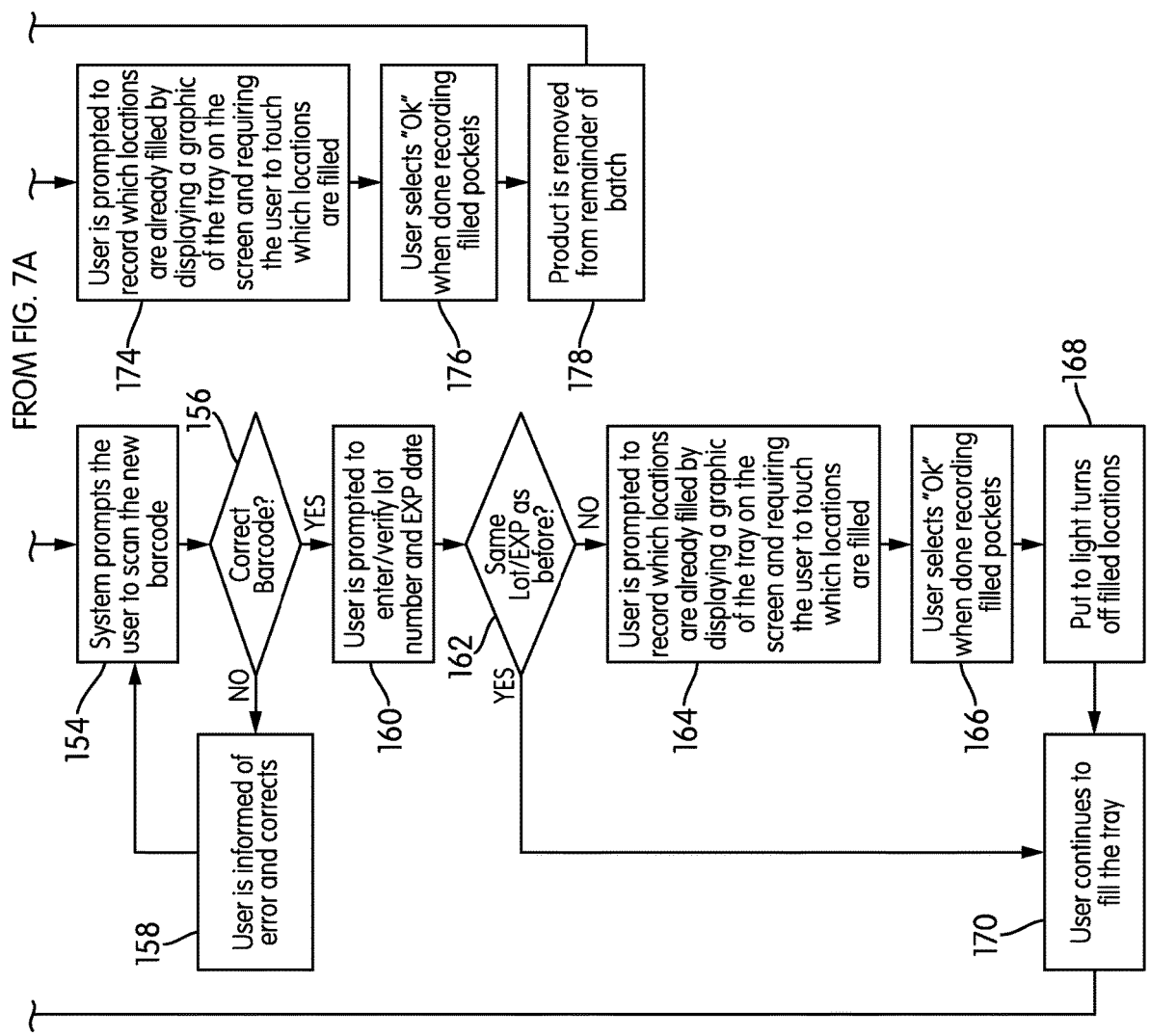

Referring to FIGS. 7A and 7B, operation of workstation 40 to fill one or more trays 20 is shown according to an exemplary embodiment. At step 100, controller 48 causes display screen 44 to display a list of each tray fill order that requires filling. Generally, the tray fill order is data received by controller 48 from database 45 providing the information needed to properly fill tray 20 using workstation 40. In one embodiment, the tray fill order includes data representative of the identity of each pharmaceutical (e.g., identity, pill size, etc.) to be filled into tray 20 and also includes data indicative of each particular of well 22 that is to receive a pharmaceutical (e.g., well ID numbers, well position numbers, etc.).

At step 102, the user selects an empty tray 20, and places the selected tray 20 onto tray support 42 of filling workstation 40. At step 104, a reading device (e.g., bar code scanner 46) reads the unique identifier of the tray 20 loaded onto tray support 42, and compares the read tray ID to database 45. At step 106, controller 48 confirms via the database check that the read tray ID has not already been assigned to a tray fill order. At step 108, if the comparison indicates that the tray 20 selected by the user has already been assigned to a tray fill order, controller 48 triggers the display of an error message on display screen 44 instructing the user of filling workstation 40 to select another tray. In one embodiment, at step 108, controller 48 triggers the display of the error message on display screen 52 located below tray 20.

If the selected tray 20 has not already been assigned a tray fill order, an unfilled tray fill order (e.g., the next tray order in the queue to be filled) is assigned to the tray (e.g., by associating the tray fill order with the tray ID in the database), and the process moves to step 110. In the various embodiments discussed herein, the tray fill order includes a list of each pharmaceutical to be filled into a particular tray 20 along with the assigned well 22 of the tray 20 that will contain a particular pharmaceutical after filling. At step 110, controller 48 displays information identifying the first pharmaceutical to be filled into tray on display screen 44 and also displays a prompt directing the user to retrieve the container holding the first pharmaceutical from a storage location (e.g., a shelf, drawer, etc.). In one embodiment, at step 110 information identifying the location of the first pharmaceutical may also be displayed.

After retrieval of the first pharmaceutical, the user scans the bar code on the pharmaceutical container using bar code scanner 46 of workstation 40. At step 112, controller 48 compares the scanned bar code to the expected bar code for the first pharmaceutical. If the scanned bar code does not match the expected bar code, at step 114, controller 48 displays an error message on display screen 44 and/or on display screen 52, and the user is prompted to retrieve the proper pharmaceutical container. If the scanned bar code matches the expected bar code, controller 48 determines that the user has selected to the proper pharmaceutical container, and at step 116, controller 48 displays a prompt to the user via display screen 44 instructing the user to enter the lot number and expiration date of the pharmaceutical (e.g., input received via keyboard associated with workstation 40 or via a touch screen version of display screen 44). In one embodiment, the lot number and/or expiration date of the pharmaceutical entered at step 116 is stored in database 45 and is associated with each tray well that holds the pharmaceutical. In this embodiment, packaging cabinet 10 has access to and may utilize the lot number and/or expiration date data during packaging of pharmaceutical. In one such embodiment, cabinet 10 is configured to access database 45 during packing of pharmaceuticals from tray 16 and to print or otherwise adhere a label onto the pharmaceutical package or pouch that indicates the lot number and/or the expiration date.

At step 118, controller 48 controls display 52 to display information (e.g., image information, alphanumeric information, etc. as discussed above) indicative of the first pharmaceutical beneath each well 22 of tray 20 that is assigned to receive the first pharmaceutical by the tray fill order. Because the bottom walls of the wells 22 of tray 20 are transparent, the user is able to see which wells 22 are highlighted by the display of information, and the user fills each highlighted well with the first pharmaceutical.

At step 120, controller 48 and/or the user determines whether there is a sufficient quantity of the first pharmaceutical within the container retrieved by the user to fill each of the wells 22 of tray 20 that are to be filled with the first pharmaceutical. If it is determined that the container retrieved by the user does not contain enough of the first pharmaceutical to fill each of the wells, the process moves to the step 150, discussed below. If it is determined that the container retrieved by the user does contain enough of the first pharmaceutical to fill each of the wells that should be filled with the first pharmaceutical, the user fills all of the wells 22 highlighted by the display of information as discussed above.

At step 122, the user indicates that each well 22 has been filled, for example by selecting a "done filling" button displayed on screen 44 (e.g., via selection by a mouse, or selection of a button on a touch screen version of screen 44). In an embodiment in which tray 20 is configured to detect filling of wells 22 using a sensor, controller 48 may be configured to automatically determine when filling is complete based on the data received from the sensors. At step 124, controller 48 stops displaying the information highlighting each of the wells 22 to be filled after controller 48 has determined that all required wells have been filled with the first pharmaceutical.

At step 126, controller 48 determines whether there are additional pharmaceuticals in the tray fill order that need to be added to the tray 20 currently located at fill workstation 40. If there are unfilled items in the tray fill order, steps 110-124 are repeated until all of the pharmaceuticals of the tray fill order have been added to the tray.

Referring to FIG. 7A, controller 48 determines that all pharmaceuticals of a tray fill order have been placed into tray 20 when the user indicates that the final pharmaceutical in the order has been filled into the tray. When controller 48 determines that filling of tray 20 is completed, at step 130, controller 48 determines whether additional quality checking or witness checking is needed. In an embodiment where no additional checking is required, the process moves to step 140, and controller 48 controls display 44 and/or display 52 to display a message that filling is completed and displays a prompt that the user is to remove the filled tray 20 from workstation 40. The user then uses the filled tray 20 to fill drawer 16 of cabinet 10, as discussed above.

In an embodiment, shown in FIG. 7A, controller 48 is configured to require additional review of the filled tray 20 prior to allowing tray 20 to be used to fill drawer 16. In this embodiment, at step 132, controller 48 controls display 44 to display a prompt to have the user of workstation 40 have a reviewer or witness login into filling workstation 40, and at step 134, the witness logs into workstation 40. At step 136, the witness sequentially selects each of the pharmaceuticals in the fill tray order (e.g., via touch screen display 44, via selection of drug name on screen via mouse), and as each different pharmaceutical is selected, controller 48 triggers the display of the information (e.g., images 62 or alphanumeric information 66 shown in FIG. 6) beneath each well of tray 20 that is supposed to contain the selected pharmaceutical. This allows the witness to confirm or double check that the appropriate pharmaceutical has been placed in the appropriate wells 22 of tray 20. At step 138, the witness confirms that tray 20 has been properly filled by selecting a tray approved icon displayed on screen 44. After the witness approves the tray, the process moves to step 140, and controller 48 controls display 44 and/or display 52 to display a message that filling is completed and displays a prompt that the user is to remove the filled tray 20 from workstation 40. The user then uses the filled tray 20 to fill drawer 16 of cabinet 10 as discussed above.

Referring back to step 120, controller 48 and/or the user determines whether there is a sufficient quantity of the first pharmaceutical within the container retrieved by the user to fill each of the wells 22 of tray 20 that are to be filled with the first pharmaceutical. If it is determined that the container retrieved by the user does not contain enough of the first pharmaceutical to fill each of the wells, the process moves to step 150. At step 150, controller 48 and/or the user checks information regarding the current inventory and if there are other containers of the needed pharmaceutical available in the inventory, controller 48 causes the display of a prompt on screen 44 instructing the user to retrieve another container of the first needed pharmaceutical from a storage location. In one embodiment, controller 48 causes the display of information indicative of the storage location of the additional container. At step 152, the user indicates that the new container of the pharmaceutical has been retrieved by selecting a start new bottle icon displayed on screen 44.

Referring to FIG. 7B, at step 154, controller 48 controls display 44 to display a prompt to the user to scan the bar code on the pharmaceutical container using bar code scanner 46 of workstation 40. At step 156, controller 48 compares the scanned bar code to the expected bar code for the first pharmaceutical. If the scanned bar code does not match the expected bar code, at step 158, controller 48 displays an error message on display screen 44 and/or on display screen 52, and the user is prompted to retrieve the proper pharmaceutical container to be filled. If the scanned bar code matches the expected bar code, controller 48 determines that the user has selected to the proper pharmaceutical container, and at step 160, controller 48 displays a prompt to the user via display screen 44 instructing the user to enter the lot number and expiration date of the pharmaceutical (e.g., via keyboard associated with workstation 40 or via a touch screen version of display screen 44). At step 162, controller 48 compares the lot number and expiration date of the new prescription container entered at step 160 to the lot number and expiration date entered at step 116. If at step 162, controller 48 determines that the lot numbers and expiration dates are the same, at step 170, controller 48 causes display 44 to display a prompt for the user to continue filling the tray, and the process passes back to step 120, and the rest of the tray is filled as discussed above.

If at step 162, controller 48 determines that the lot numbers and expiration dates are different, at step 164, controller 48 causes screen 44 to display a prompt instructing the user to identify which wells 22 of tray 20 where already filled with the pharmaceutical. In one embodiment, controller 48 cause the display of an image of tray 20 on screen 44, and the user selects (e.g., via touch screen display 44, or via selection of the wells on the screen via a mouse), which wells of the tray were already filled. At step 166, when the user has selected all of the wells that were filled from the original pharmaceutical container, the user indicates completion by selecting an ok or step completed icon. At step 168, controller 48 stops the display information (e.g., images 62, alphanumeric information 66, etc.) on screen 52 beneath the wells 22 that were already filled but continues to display information (e.g., images 62, alphanumeric information 66, etc.) on screen 52 beneath the wells 22 that still must be filled with the pharmaceutical from the new container. Thus, after step 168, controller 48 only causes the display of information (e.g., images 62, alphanumeric information 66, etc.) on screen 52 beneath the wells 22 that still need to be filled, and then at step 170, controller 48 causes display 44 to display a prompt for the user to continue filling the tray, and the process passes back to step 120, and the rest of the tray is filled as discussed above.

Following step 150, at step 172, if no additional containers of the needed pharmaceutical are available, the user selects an icon indicating that no additional containers of the needed pharmaceutical are available. In one embodiment, controller 48 accesses inventory information directly to determine whether additional containers of the needed pharmaceutical are available, and in this embodiment, step 172 is skipped. At step 174, controller 48 causes screen 44 to display a prompt instructing the user to identify which wells 22 of tray 20 where already filled with the pharmaceutical. In one embodiment, controller 48 causes the display of an image of tray 20 on screen 44, and the user selects (e.g., via touch screen display 44, or via selection of the wells on the screen via a mouse) which wells of the tray were already filled with the needed pharmaceutical. At step 176, when the user has selected all of the wells that were filled from the original pharmaceutical container, the user indicates completion by selecting an ok or step completed icon. However, in an embodiment in which the wells of tray 20 are equipped to sense filling of the wells (e.g., via a touch sensitive bottom wall, etc. as discussed above), controller 48 may be configured to automatically determine that the wells have been filled based upon the data from the sensors. The information captured at step 174 and 176 is used by controller 48 and/or the control system of cabinet 10 to track which wells of tray 20 and of drawer 16 were not able to be filled as requested by the fill tray order. At step 178, the pharmaceutical that is out of stock is removed from the fill tray order, and the process passes back to step 126, and filling of the tray continues as discussed above.

As an alternative to the use of separate display device 52 and non-opaque, moveable well closure panels, it is also contemplated that display device 52 could be modified to also function as the closure panel. For example, a moveable, LED display panels could be used as the closure panels to eliminate the separate display device 52 and the need to index the tray to the display device. In this embodiment, the tray would include a wired or wireless interface to the workstation so that LED closure panels of the trays 18 could be controlled by the workstation 40 to generate the images required below each well 22. Additionally, this configuration may permit the elimination of the use of a barcode as the tray identifier. Rather, the tray identifier would be a code stored in the tray and read by the workstation 40 through the interface.

Figure 8:
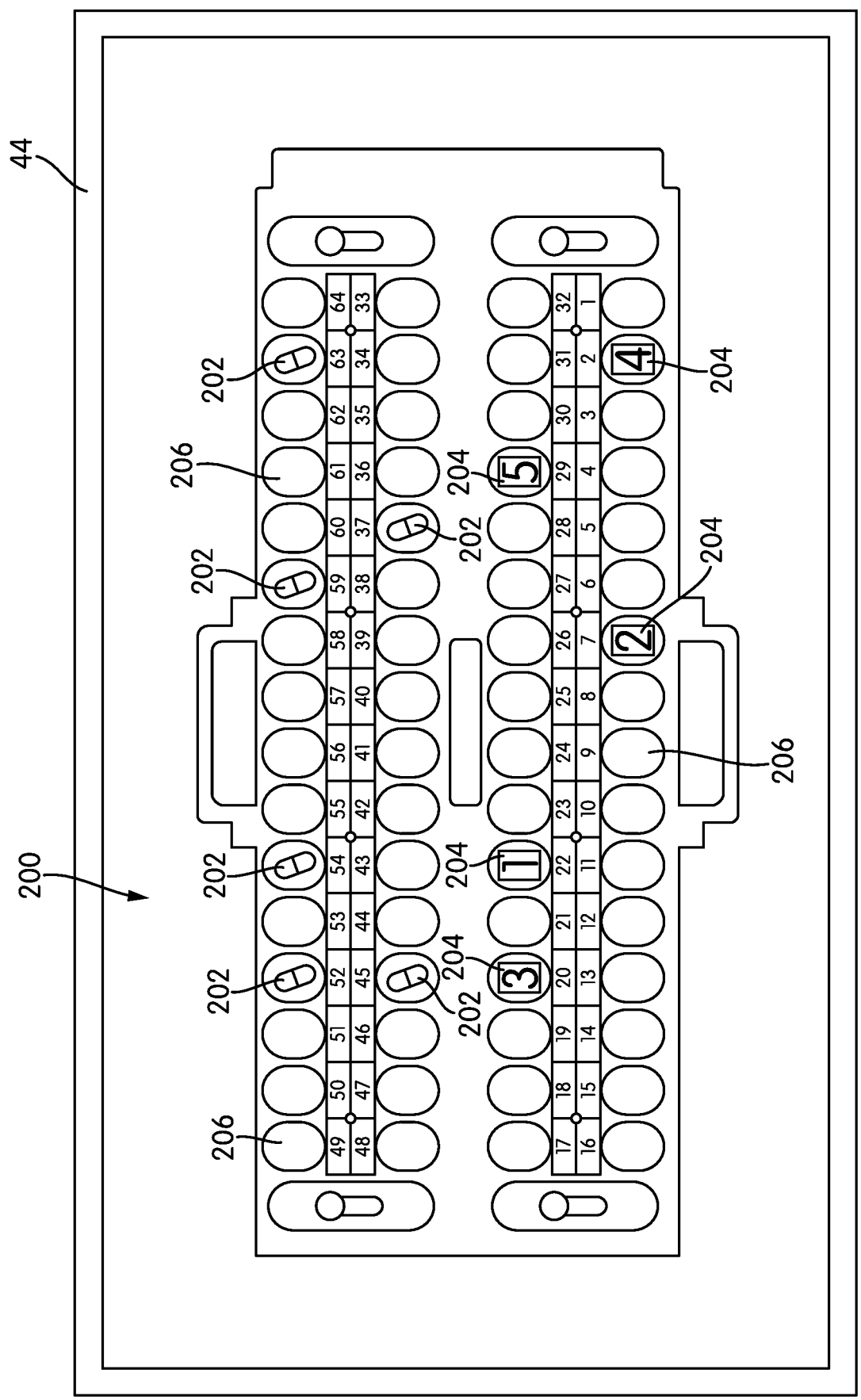
FIG. 8 is a display of a pharmaceutical tray according to an exemplary.

Referring to FIG. 8, in another embodiment, workstation 40 may be configured to display information representative of pharmaceuticals to be filled into tray 20 on a display screen (for example display screen 44) located adjacent to a tray 20 to assist the user in properly filling the wells of tray 20. In one such embodiment, workstation 40 is configured to facilitate filling of a tray 20 by displaying an image 200 representative of a tray 20 to be filled on the display screen 44 of workstation 40. In this embodiment, the display of the graphic 200 is adjacent the wells 22 of tray 20 due to the proximity of tray 20 to display 44 during filling. Image 200 replicates includes graphics 206 representative of each of the wells 22 of tray 20, and each of the well graphics 206 have a spatial relationship to the other wells and to the other displayed structure that correlates to the spatial relationship of wells 22 and the structure of physical tray 20. In one embodiment, image 200 is a to scale graphical representation of tray 20.

In various embodiments, controller 48 is configured to alter the display of graphics on display 44 to facilitate the filling of tray 20. For example, in one embodiment, controller 48 is configured to display images of pharmaceuticals to be filled, for example images 202, within one or more well graphics 206 of image 200 that correlate to the wells 22 of tray 20 that are to receive a particular pharmaceutical. In another embodiment, controller 48 is configured to display alphanumeric information of pharmaceuticals to be filled, for example images 204, within one or more well graphics 206 of image 200 that correlate to the wells 22 of tray 20 that are to receive a particular pharmaceutical. In another embodiment, controller 48 is configured to display other graphics (e.g., change color, highlight, display "fill", etc.) within or around one or more well graphics 206 of image 200 that correlate to the wells 22 of tray 20 that are to receive a particular pharmaceutical.

In this embodiment, graphic 200 on display 44 acts as a map or graphical directions to the user of workstation 40 regarding how tray 20 should be filled. In this embodiment, the user views graphic 200 to determine which of well graphics 206 are indicated (e.g., via graphics 202, alphanumeric info 204, or other highlighting) to receive a pharmaceutical. The user correlates the indicated well graphics 206 with the physical wells 22 in tray 20, and fills wells 22 accordingly. In this manner, controller 48 and the user substantially execute the method shown in FIGS. 7A and 7B except that steps 118, 124 and 168 involve the display of graphics 202 or 204 within well graphics 206 on display 44 rather than the display on screen 52 as discussed above.

It should be understood that the figures illustrate the exemplary embodiments in detail, and it should be understood that the present application is not limited to the details or methodology set forth in the description or illustrated in the figures. It should also be understood that the terminology is for the purpose of description only and should not be regarded as limiting.

Further, as used herein pharmaceutical items includes drugs, medicines, over the counter drugs, prescription drugs, nutritional supplements, nutraceuticals, tablets, powders, or any other similar product that may be used in a health care setting. In addition, medical items may include pharmaceutical items, medical devices, medical instruments, medical supplies (e.g., bandages, syringes, gauze, IVs, ampules, ports, etc.).

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above.

What is claimed is:

1. A system for facilitating the manual filling of a pharmaceutical tray including at least two wells configured to hold a pharmaceutical, the system comprising:
    an electronic display device configured to display information adjacent to the at least two wells of the pharmaceutical tray, wherein the electronic display device is positioned substantially horizontally;
    a controller configured to control the electronic display device to display information representative of a first type of pharmaceutical adjacent to a first well to direct manual placement of the first type of pharmaceutical into the first well and to control the electronic display device to selectively display information representative of a second type of pharmaceutical adjacent to a second well to direct manual placement of the second type of pharmaceutical into the second well; and
    a support structure that supports the pharmaceutical tray above the substantially horizontal electronic display device.

2. The system of claim 1 wherein the displayed information representative of the first type of pharmaceutical is at least one of an image of the first pharmaceutical and alphanumeric information identifying the first pharmaceutical, and wherein the displayed information representative of the second type of pharmaceutical is at least one of an image of the second pharmaceutical and alphanumeric information identifying the second pharmaceutical.

3. The system of claim 1 wherein the electronic display device is a flat panel display screen.

4. The system of claim 3 further comprising a second screen display, wherein the controller is configured to control the second screen display to receive input from a user and to display instructions that guide the user filling the pharmaceutical tray.

5. The system of claim 3, wherein the support structure is positioned around the peripheral edge of the electronic display device and configured to support the pharmaceutical tray above the electronic display device.

6. The system of claim 3 wherein the controller is configured to display a graphic representative of the pharmaceutical tray including well graphics representative of the first well and the second well, wherein the controller is configured to display graphical information to highlight the first well and the second well within the displayed graphic representative of the pharmaceutical tray.

7. A system for facilitating the manual filling of a pharmaceutical tray including at least two wells each configured to hold a pharmaceutical, the system comprising:
    an electronic display device configured to display information adjacent to the at least two wells of the pharmaceutical tray, wherein the electronic display device is a flat panel display screen;
    a controller configured to control the electronic display device to display information representative of a first type of pharmaceutical adjacent to a first well to direct manual placement of the first type of pharmaceutical into the first well and to control the electronic display device to selectively display information representative of a second type of pharmaceutical adjacent to a second well to direct manual placement of the second type of pharmaceutical into the second well; and
    a support structure around the peripheral edge of the flat panel display screen configured to support the pharmaceutical tray above the flat panel display screen, wherein the flat panel display screen is positioned substantially horizontally such that the flat panel display screen is viewable from a position above the flat panel display screen.

8. The system of claim 7 wherein the displayed information representative of the first type of pharmaceutical is at least one of an image of the first pharmaceutical and alphanumeric information identifying the first pharmaceutical, and wherein the displayed information representative of the second type of pharmaceutical is at least one of an image of the second pharmaceutical and alphanumeric information identifying the second pharmaceutical.

9. The system of claim 7 further comprising a second screen display, wherein the controller is configured to control the second screen display to receive input from a user and to display instructions that guide the user filling the pharmaceutical tray.

10. The system of claim 7 wherein the controller is configured to display a graphic representative of the pharmaceutical tray including well graphics representative of the first well and the second well, wherein the controller is configured to display graphical information to highlight the first well and the second well within the displayed graphic representative of the pharmaceutical tray.

* * * * *